June 23, 1964 H. M. EDDIE Plant Pat. 2,413
DOGWOOD PLANT
Filed Nov. 7, 1962
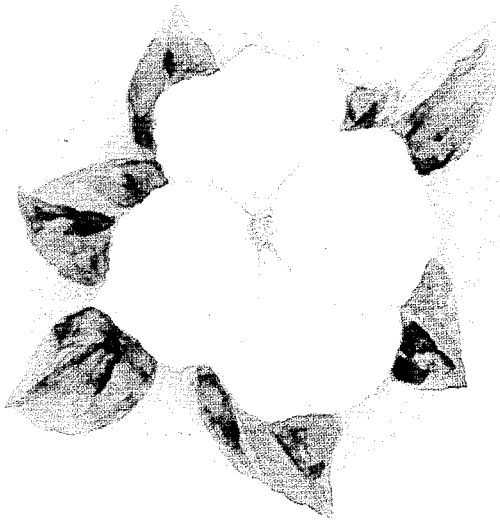
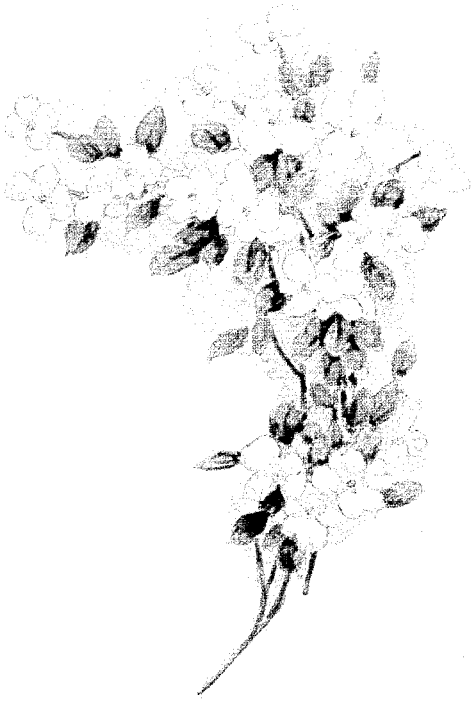
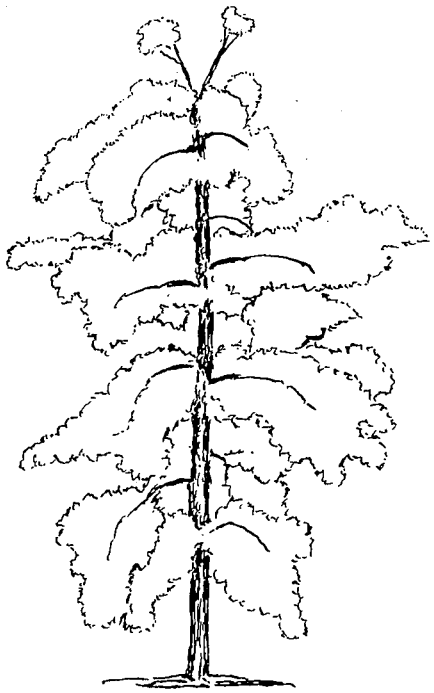
WITNESS
Addison E. Avery
INVENTOR
Henry Matheson Eddie, deceased,
by J. Henry Eddie, Executor,
by John H. Graves Jr.,
ATTY.

United States Patent Office

Plant Pat. 2,413
Patented June 23, 1964

2,413
DOGWOOD PLANT

Henry Matheson Eddie, deceased, late of Vancouver, British Columbia, Canada, by J. Henry Eddie, executor, Vancouver, British Columbia, Canada, assignor to The Wayside Gardens Company, Mentor, Ohio Filed Nov. 7, 1962, Ser. No. 236,175
1 Claim. (Cl. Plt.—51)

This invention relates to a new hybrid dogwood plant.

The present plant was produced by the decedent by crossing *Cornus nuttalli* as the seed or pistillate parent and *Cornus florida rubra* as the pollen or staminate parent. The *Cornus nuttalli* is native to the Pacific coast and the *Cornus florida rubra* is a pink form of the native eastern dogwood.

The new variety was first asexually reproduced by the decedent in Sardis, British Columbia, by budding.

The drawings illustrate the new variety, showing at the top center a single bloom and surrounding leaves in color, at the lower left-hand a spray of branches with leaves and blooms, all in color, and at the lower right a black and white sketch illustrating the unusual contour of the tree.

Color references are to the Maerz and Paul Dictionary of Color.

*Exposed Plant Structure*

The exposed plant is a hardy, woody tree characterized by an upright trunk with branches extending generally horizontally therefrom and slightly pendent at their outer extremities. The shape of the tree is generally erect and somewhat tall and pyramidal, as distinguished from the relatively low tops of other types of dogwood trees which tend to spread and have relatively flat tops. For example, a 10 year tree is about 12 feet high and about 4 to 5 feet wide, with a trunk about 5 inches in diameter.

The present tree is taller than the scrubby dogwoods such as *C. stolonifera, kousa,* and *sanguinea,* but it is believed not likely to attain the height of *Cornus nuttalli,* or even *Cornus florida,* because of its more drooping habit of growth. No mature specimens of the present tree exist, but a study and comparison of the oldest specimen, twelve years of age in 1963, with the other dogwoods makes it appear that the new hybrid will be more compact and smaller than *Cornus florida* when fully grown, possibly reaching a maximum height of 35 feet.

Asexually reproduced specimens of the plant have been observed in Sardis, British Columbia, in Mentor, Ohio, and at the Arnold Arboretum at Boston, Massachusetts. The twelve year old specimen is about 14 feet in height. In the same localities, mature *Cornus nuttalli* trees reach a height of from 40 to 70 feet and mature *Cornus florida* trees a height of from 20 to 40 feet.

Its rate of growth is medium. It appears to be hardier than the *Cornus nuttalli,* and comparable in hardiness to *Cornus florida* grown in the same areas in British Columbia and in Mentor, Ohio.

It has good resistance to drought and wet seasons. An inspection of numerous test specimens over a period of 10 years has disclosed no disease or insect infestation. The tree grows well in sun or shade in normal, average soil.

*Individual Parts of Exposed Plant*

The main trunk is upright with branches generally horizontal, but slightly pendent at their outer ends with somewhat recumbent tips. The branching is average for Cornus plants, being of average toughness and generally adequate to support the foliage, blooms, and fruit well.

The branches are somewhat greenish on the underside with a bronze cast on the upper side. They are oppositely arranged and have a smooth texture. They are relatively flexible and slightly curving.

The main trunk has a somewhat greyish cast.

The foliage is relatively dense with the leaves in whorled arrangement. The leaves are about medium size. Both the old and new leaves are green on the top and bottom, the color being relatively uniform.

The leaves range from about 2 inches minimum length to about 4 inches maximum length and from 1¼ inches minimum width to about 3 inches maximum width. The mature leaves are almost round, whereas the young leaves are obovate. All are relatively thin and have entire margins. The upper faces are a rough, flat green. The persistency of the leaves on the plant is outstanding and excellent, being comparable to those of the *Cornus florida* in the same locations.

The stems are green and relatively short with a smooth texture and medium strength.

The plant blooms well in Sardis, British Columbia, in Mentor, Ohio, and in Boston, Massachusetts. The asexually reproduced specimens have withstood winter temperatures as low as 5° F. below zero in British Columbia and as low as 22° F. below zero in Mentor, Ohio. The observed specimens have been growing in Sardis, British Columbia, and in Mentor, Ohio, for five or six years. During this period, the lowest winter temperatures generally occurring in Mentor, Ohio were about 10° F. below zero, except for one winter when the temperature dropped to 22° F. below zero. Likewise, it blooms well in average soil in fairly sunny locations. It is not particular as to sun, shade, or exposure. For most effective blooming it prefers a slightly acid, sandy or clay loam. It tends to produce a reduced number of flowers when the tree is grown in the shade. Likewise, their color is not as desirable as it is when grown in the sun.

The plant blooms continuously from about May 1 to May 25th, in Sardis, British Columbia, and from about May 15th to June 10th in Mentor, Ohio, and the blooms last quite well on the tree.

The flower buds are intermediate in size with respect to the parents, and are globular and smooth surfaced. They are supported in generally upright position. When the flowers begin to bloom, the bracts are somewhat greenish, turning to a cream white as they open, and when half bloom they become very white.

The bloom, that is the flower head plus the bracts, averages about 4 inches to 6 inches in diameter and hundreds are borne on an average plant 10 years of age. They are borne singly. Their permanence is average both on the plant and when cut. The so-called petalage comprises four bracts which are very white.

The bracts, which are the spectacular part of the flower, are much larger than those of *Cornus florida,* resembling in form and size the *Cornus nuttalli.* In British Columbia, the bracts are 5 inches or more long. In the same locality, under like conditions, *Cornus florida* and *florida rubra* have bracts which are ovate and from 1½ to 2 inches long.

The true flower, that is, the bloom without the bracts, is similar to that of its parents, but is smaller than *Cornus nuttalli,* which is usually about ¾ inch in diameter, and about the same size as the *Cornus florida,* which is usually about ½ inch in diameter.

The tips of the bracts have a faint touch of pink comparable to Plate 1–F–7. The center of the blossom is a brownish red comparable to Plate 13–L–9. The bracts are white. The leaves are green comparable to Plate 21–L–8. The general tonality from a distance is white. The color varies only slightly from the time that they are full blown until they are ready to fall. The blooms last for about 10 days after they are fully developed, turning brown or slightly pinkish at the tips with age. Their texture is similar to that of the *Cornus nuttalli.* In appearance, the bloom is symmetrical and flat with slight crinkling. All of the flowers include four bracts arranged in overlapping relation, as illustrated in the top view in the drawings.

The stamens are numerous and generally brownish-red. They are plentiful with short filaments. The pollen color is light cream.

The fruit is similar to that of the *Cornus nuttalli* except that in general the tree bears very few fertile fruits. The fruit is about medium size and without a stem. The skin is relatively tough. The flesh is firm at the surface but mealy inside. The fruits are borne in groups, the kernel itself being about 3/16 inches to 1/4 of an inch long.

This hybrid partakes of some of the characteristics of both of its parents. The flower bract is similar in size and shape to that of the *Cornus nuttalli,* but the stamens are about half the overall size of those of the *nuttalli,* being more like those of the *Cornus florida.* The leaves are like those of the *Cornus nuttalli,* but have some characteristics of the *Cornus florida.* The leaf twigs and young branches resemble those of the *Cornus florida.*

An outstanding characteristic of the plant is that the tree combines the finer qualities of both parents. It combines the larger flowers of the *Cornus nuttalli* with the excellent autumn color of the leaves of the *Cornus florida.* Further, the overall shape of the tree is unusual for a dogwood tree, in that the branches start out horizontally from the trunk, becoming pendent and slightly recurvent at their outer ends. The tree, in general, is characterized in that it has a pyramidal shape, peaked at the top. It appears to be more compact than the *Cornus florida,* and has a drooping habit of growth. The blooms are very large and the blooming period is unusually long.

Having thus shown and described the new variety of Cornus plant, what is claimed is:

A new and distinct variety of Cornus plant substantially as herein shown and described.

No references cited.